US010022109B2

(12) United States Patent
Lücke et al.

(10) Patent No.: US 10,022,109 B2
(45) Date of Patent: Jul. 17, 2018

(54) DETECTION DEVICE FOR THE IN VIVO AND/OR IN VITRO ENRICHMENT OF SAMPLE MATERIAL

(75) Inventors: Klaus Lücke, Potsdam OT Golm (DE); Andreas Bollmann, Potsdam OT Golm (DE); Steffi Mewes, Potsdam OT Golm (DE); Robert Niestroj, Potsdam OT Golm (DE)

(73) Assignee: GILUPI GMBH, Potsdam OT Golm (DE)

( * ) Notice: Subject to any disclaimer, the term of this patent is extended or adjusted under 35 U.S.C. 154(b) by 1107 days.

(21) Appl. No.: 13/143,103

(22) PCT Filed: Jun. 17, 2010

(86) PCT No.: PCT/EP2010/003644
§ 371 (c)(1),
(2), (4) Date: Jun. 1, 2012

(87) PCT Pub. No.: WO2010/145824
PCT Pub. Date: Dec. 23, 2010

(65) Prior Publication Data
US 2012/0237944 A1    Sep. 20, 2012

(30) Foreign Application Priority Data

Jun. 17, 2009 (EP) .................... 09075271

(51) Int. Cl.
*A61B 10/00* (2006.01)
*G01N 33/543* (2006.01)
*A61B 10/02* (2006.01)

(52) U.S. Cl.
CPC .......... *A61B 10/0045* (2013.01); *A61B 10/02* (2013.01); *G01N 33/543* (2013.01); *G01N 33/54366* (2013.01)

(58) Field of Classification Search
CPC ............ G01N 33/543; G01N 33/54366; A61B 10/0045; A61B 10/02
(Continued)

(56) References Cited

U.S. PATENT DOCUMENTS 6,245,029 B1 *   6/2001   Fujita et al. .................. 600/585
7,645,504 B1 *   1/2010   Pacetti ..................... A61L 31/10
                                                           427/2.1
(Continued)

FOREIGN PATENT DOCUMENTS

CN    101019027 A    8/2007
CN    101305280 A    11/2008
(Continued)

OTHER PUBLICATIONS

International Search Report (PCT/ISA/210) dated Sep. 29, 2010, by Japanese Patent Office as the International Searching Authority for International Application No. PCT/EP2010/003644.
(Continued)

*Primary Examiner* — Melanie Yu Brown
(74) *Attorney, Agent, or Firm* — Buchanan Ingersoll & Rooney, PC

(57) ABSTRACT

The present invention refers to a detection device for the in vivo and/or in vitro enrichment of sample material, the detection device comprising a functional surface equipped with detection receptors. To further improve the enrichment of sample material by using a detection device of the aforementioned type, it is provided according to the invention that the functional surface has a three-dimensional structure with mutually facing functional sections which form spaces that can be filled with a sample liquid. Furthermore, the present invention provides for a use and for a method for the use of the detection device.

13 Claims, 1 Drawing Sheet

(58) Field of Classification Search
USPC .......................................................... 435/7.1
See application file for complete search history.

(56) References Cited

U.S. PATENT DOCUMENTS

| | | | |
|---|---|---|---|
| 8,183,057 B2* | 5/2012 | Isojima et al. ................ | 436/518 |
| 2002/0006656 A1 | 1/2002 | Holloway | |
| 2002/0155113 A1 | 10/2002 | Chun et al. | |
| 2005/0021131 A1* | 1/2005 | Venkatraman ............ | A61F 2/82 |
| | | | 623/1.19 |
| 2005/0136258 A1 | 6/2005 | Nie et al. | |
| 2005/0282182 A1* | 12/2005 | Tajima ................. | C12Q 1/6837 |
| | | | 435/6.11 |
| 2006/0051265 A1 | 3/2006 | Mohamed et al. | |
| 2007/0191932 A1 | 8/2007 | Kutryk et al. | |
| 2008/0044925 A1 | 2/2008 | Isojima et al. | |
| 2008/0213130 A1 | 9/2008 | Pison et al. | |
| 2008/0311281 A1* | 12/2008 | Andreacchi ......... | B05B 13/0442 |
| | | | 427/2.25 |
| 2009/0081427 A1* | 3/2009 | Kuruma ............ | B01L 3/502715 |
| | | | 428/209 |
| 2009/0117097 A1* | 5/2009 | Igawa et al. ................ | 424/130.1 |
| 2009/0131274 A1 | 5/2009 | Pison et al. | |
| 2009/0269778 A1 | 10/2009 | Margraf et al. | |
| 2010/0168609 A1* | 7/2010 | Pison et al. .................. | 600/562 |
| 2011/0130680 A1* | 6/2011 | Dahlstrand ......... | A61B 10/0233 |
| | | | 600/567 |
| 2012/0053078 A1 | 3/2012 | Isojima et al. | |

FOREIGN PATENT DOCUMENTS

| | | | |
|---|---|---|---|
| CN | 101421623 A | | 4/2009 |
| CN | 101437853 A | | 5/2009 |
| WO | 2003065881 A2 | | 8/2003 |
| WO | WO 2006/131400 A1 | | 12/2006 |
| WO | 2010025719 A1 | | 3/2010 |

OTHER PUBLICATIONS

E. Florek et al., "The acute systemic toxicity study for normal catheter and cell-select catheter (CSC)", Archives of Perinatal Medicine, 2008 (month unknown), pp. 20-31, vol. 14, No. 2.

Office Action (Communication pursuant to Article 94(3) EPU) dated Nov. 13, 2013 by the European Patent Office in corresponding European Patent Application No. 10 725 395.7-1405. (4 pages).

Office Action dated Feb. 13, 2014, by the Chinese Patent Office in corresponding Chinese Patent Application No. 201080027208.2 and an English translation of the Office Action. (25 pages).

International Search Report (PCT/ISA/210) dated Sep. 29, 2010, by European Patent Office as the International Searching Authority for International Application No. PCT/EP2010/003644.

Ewa Florek et al., The acute systemic toxicity study for normal catheter and cell-select catheter (CSC).

EPO communication dated May 28, 2014, by the EPO in corresponding EPO Application No. 10 725 395.7-1405.2 a (5 pages).

Firkowska et al., "Biocompatible Nanomaterials and Nanodevices Promising for Biomedical Applications", Nanomaterials for application in Medicine and Biology, Jan. 1, 2008, Springer Netherlands, Dordrecht, XP055119345, ISSN: 1874-6500 (1-15 pages).

Office Action dated Aug. 29, 2014, by the Chinese Patent Office in corresponding Chinese Patent Application No. 2010800272081, and an English Translation of the Office Action. (19 pages).

Office Action dated Mar. 25, 2015, by the Chinese Patent Office in corresponding Chinese Patent Application No. 2015032001261920, and an English Translation of the Office Action (8 pages).

* cited by examiner

DETECTION DEVICE FOR THE IN VIVO AND/OR IN VITRO ENRICHMENT OF SAMPLE MATERIAL

The present invention relates to a detection device for the in vivo and/or in vitro enrichment of sample material, the detection device comprising a functional surface equipped with detection receptors.

Although many cell types, molecules, tumor markers and biomarkers are present in body fluids, it is often not possible to obtain them—on account of their low concentration—in an adequately efficient way with the conventional enrichment methods so as to use them later in established diagnostic methods of clinical chemistry, pathology and cytology.

For instance, it is possible to enrich special cells, particularly circulating tumor cells, from a blood sample (in vitro) by means of commercially available paramagnetic nanoparticles and/or by density gradient centrifugation, but only in a very limited number and with the drawback that the nanoparticles bind to or in the cell and might thus damage them or complicate diagnosis. One of these commercial methods lies in a test in which e.g. circulating tumor cells from 7.5 ml blood volume are enriched by means of paramagnetic nanoparticles to be then able to make statements on the progress of the disease.

The restrictive factor of this method is the obtained sample volume which is many times greater when a detection device is used for the in vivo enrichment of sample material, e.g. a functionalized catheter. Vascular catheters for the application of medical interventions have a cylindrical design most of the time. The advantage of such a shape is the relatively low friction resistance. Nevertheless this shape poses the risk that the bloodstream is constricted in small blood vessels and that this might cause thrombosis.

It is the object of the present invention to further improve the enrichment of sample material by using a detection device of the aforementioned type.

To achieve the object underlying the present invention, a detection device is provided for the in vivo and/or in vitro enrichment of sample material, the detection device comprising a functional surface equipped with detection receptors, wherein the functional surface has a three-dimensional structure with mutually facing functional sections which form spaces that can be filled with a sample liquid. Within the scope of the invention the functional sections are regarded as mutually facing if they enclose an angle of less than 180°, i.e. when they can "see" each other. As a consequence, the detection device according to the invention has a greater functional surface in comparison with a conventional detection device having a smooth or cylindrical functional surface. Furthermore, the sample liquid can be passed into the spaces ideally via the functional surface and enriched on the detection receptors. Moreover, the ligands docking to the detection receptors can be retained in the spaces, whereby they are better protected from abrasion. Preferably, the functional surface can also store a certain volume of sample liquid. The mutually facing functional sections can be equipped with chemically identical or chemically different detection receptors. Hence, in case of need different ligands can also be enriched in an application. Within the meaning of this invention all structures, particularly receptors or ligands, which are suited for capturing target molecules and target cells are called detection receptors. Furthermore, all target molecules and target cells that can dock to the detection receptors are just called ligands. The term sample liquid designates a sample present in liquid form.

Preferred developments of the invention are the subject matters of the sub-claims.

It may be helpful when the functional surface is three-dimensionally structured in the macroscopic and/or microscopic range. Due to a functional surface which is three-dimensionally structured in the macroscopic or visible range and which is e.g. determined by the visible geometry of the detection device, the sample liquid can be passed in an advantageous manner over the functional surface. Due to the functional surface which is three-dimensionally structured in the microscopic range the flow velocity can be reduced in the area of the interface. The spaces are preferably dimensioned at least in such a manner that specific ligands can dock to the detection receptors. Preferably, the spaces are dimensioned such that approximately the number of specific ligands that corresponds to the number of the detection receptors on the mutually facing functional sections can be received and arranged. The functional surface can thereby be used in an ideal manner. Furthermore, the ligands can be protected against abrasion in an even better way.

In an advantageous configuration of the invention the space is channel-shaped at least in sections, with several spaces preferably forming a complex network of channels. The channel can extend over the whole length of the functional surface. Sample liquid can thereby be passed to the detection receptors in an ideal way. Flow velocity and flow direction of the sample liquid can be influenced through the configuration of the size of the spaces. Preferably, the channel extends at least in sections in the longitudinal direction of the detection device, so that the channel has the least impact on a natural flow direction of the sample liquid.

It may be of advantage when the functional surface is formed with elevations, depressions and/or ramifications and/or has at least in part a spiral, screw-shaped, worm-shaped, undulated, helical, filamentous, brush-like, comb-like, meshed, porous, sponge-like or similar structure. Such shapes have large surfaces and are well suited for use in the detection device according to the invention. Spiral, screw-shaped, worm-shaped, undulated, helical structures have a low friction resistance as a rule. The flow of the sample liquid, e.g. blood in a blood vessel, is thereby hardly impaired even if parts of the functional surface abut on the vascular walls. Filamentous, brush-like, comb-like, meshed, porous and sponge-like structures slow down the natural flow of the sample liquid and are excellently suited as a liquid reservoir, whereby the enrichment of the ligands on the detection receptors is additionally promoted.

It may turn out to be advantageous when the detection receptors comprise antibodies, antibody fragments, amino acid structures, nucleic acid structures and/or synthetic structures with a specific affinity to cell surfaces, preferably monoclonal antibodies of murine origin, chimeric antibodies or humanized antibodies, preferably HLA-G and/or EpCAM antibodies.

It may also be convenient when the functional surface comprises saturated atom groups and covalently bound ligands and receptors to prevent undesired interactions with blood components and the binding of non-specific cells and molecules.

It may further be of advantage when the detection device is formed at least in sections as a guide wire, stent and/or catheter. Such components are available at low costs and can be modified for implementing the invention.

It may turn out to be convenient when the detection device comprises a functionalized section provided with the functional surface and also a non-functionalized section, both of which are joined to form a stylet. It may be of advantage when the functionalized section and the non-functionalized section are detachably connected. Thus the functionalized section can be separated from the non-functionalized section for the period during which the detection device is e.g. introduced into a bloodstream. For instance, the functionalized section is fixed to the indwelling venous cannula and is again coupled with the non-functionalized section at a later time.

However, it may also be convenient when the non-functionalized section comprises a marking for application control and/or a rounded end as protection from injury. The detection device can thereby be controlled in a better way. Moreover, the risk of injury and infection is reduced during use of the detection device.

In an advantageous configuration of the invention the detection device comprises a carrier which preferably meets at least one of the following requirements:

The surface of the carrier is formed with elevations, depressions and/or ramifications and/or has at least in part a spiral, screw-shaped, worm-shaped, undulated, helical, filamentous, brush-like, comb-like, meshed, porous, sponge-like or similar structure. The aforementioned advantages can be achieved with such structures. The spaces on the surface of the carrier that are e.g. defined by the pore size or the thickness and amount of the filaments are such that the specific ligands can penetrate and dock to the detection receptors. Shape and design of the surface of the carrier are independent of the shape and design of a substrate of the carrier as such. The surface of the carrier can be three-dimensionally structured in the macroscopic and/or in the microscopic range.

The carrier comprises a substrate which is formed with elevations, depressions and/or ramifications and/or has at least in part a spiral, screw-shaped, worm-shaped, undulated, helical, filamentous, brush-like, comb-like, meshed, porous, sponge-like or similar structure. The aforementioned advantages can be achieved with such structures. A spiral substrate preferably comprises a strand consisting of one or plural metal wires. A brush-like substrate is preferably formed by one or plural metal, glass, Teflon or plastic polymer filaments. A screw-shaped substrate has e.g. the form of a corkscrew. Since the substrate can be coated, the shape and design of the surface of the carrier are independent of the shape and design of the substrate. The substrate can be three-dimensionally structured in the macroscopic and/or in the microscopic range.

The carrier comprises a coating of metal, preferably of a metal of the $10^{th}$ or $11^{th}$ group of the Periodic Table of Elements, preferably of nickel, copper, palladium, silver, platinum and/or gold, preferably a coating according to patent application WO 2006/131400 A1.

The carrier comprises functional groups, preferably organic functional groups, preferably sulfur- and/or nitrogen-containing functional groups, particularly preferably a coating with functional groups.

The carrier comprises a biocompatible dye, preferably a coating of a biocompatible dye, to reduce autofluorescence during microscopic analysis.

The carrier is configured as a solid body or as a hollow body. As a hollow body the carrier can comprise at least one cavity and an opening communicating with the cavity, through which the sample liquid passes into the cavity. The functional surface can be located within the cavity. Such a detection device is particularly suited for in vitro applications and serves e.g. simultaneously as a storage medium for the sample liquid, e.g. for transport.

The carrier is made from a biocompatible material. A defense reaction of the body can thereby be prevented during the in vivo use of the detection device.

The carrier consists at least in part of metal, preferably high-grade steel, medical high-grade steel or titanium; of glass, preferably glass fiber; of plastic, preferably of a foamed plastic, a polymer, preferably polyethylene, polypropylene, polyurethane, polytetrafluoroethylene, a plastic based on organic polymers, or a combination of said materials. Such materials are usually available at low costs and are flexible and easily formable.

The coating is applied by means of a galvanic process, a ceramic process, cementation or vapor deposition onto the carrier. These processes turn out to be advantageous under manufacturing aspects. The thickness of the coating is preferably within the range of 0.1 µm to 10 µm, preferably in the range of 0.2 µm to 5 µm, particularly preferably in the range of 0.5 µm to 1 µm.

The carrier comprises saturated atom groups and covalently bound ligands and receptors to prevent undesired interactions with blood components and the binding of non-specific cells and molecules.

The carrier comprises and/or forms the functional surface. The functional surface is preferably located on the surface of the carrier, the carrier comprising the mutually facing functional sections and the carrier being equipped directly with the detection receptors. To this end it is advantageous when the carrier consists of a biocompatible polymer.

In another advantageous configuration of the invention the detection device comprises a biocompatible polymer which preferably meets at least one of the following requirements:

The biocompatible polymer is formed as a coherent polymer layer. The whole surface of the carrier can thereby be covered or shielded by the polymer layer. The thickness of the polymer layer is preferably in the range of 0.1 µm to 10 µm, preferably in the range of 0.5 µm to 5 µm, particularly preferably in the range of 1 µm to 2 µm.

The biocompatible polymer has a three-dimensional, preferably filamentous and/or porous structure. Said structure forms many spaces which are substantially filled by the ligands docking to the detection receptors, so that the ligands can be protected in an even better way against abrasion. The biocompatible polymer can be three-dimensionally structured in the macroscopic and/or in the microscopic range.

The biocompatible polymer comprises a three-dimensional, preferably filamentous and/or porous surface. The surface of the biocompatible polymer can be three-dimensionally structured in the macroscopic and/or in the microscopic range.

The biocompatible polymer has a carbon-containing, branched molecular structure. This molecular structure is excellently suited for binding the detection receptors and for the enrichment of ligands on the detection receptors. Said molecular structure forms a filamentous functional surface within the meaning of the present invention that is three-dimensionally structured in the microscopic range. The branched molecular structures have numerous spaces that are formed by mutually facing functional sections equipped with detection receptors in the form of polymer molecules. These spaces can be filled with a sample liquid and can form a liquid reservoir, whereby the enrichment of the ligands on the detection receptors is particularly promoted. In the area of the interface on a surface occupied by this molecular structure the flow of a sample liquid is considerably slowed down. The enrichment of the ligands is thereby promoted in addition.

The biocompatible polymer is preferably operatively connected via functional groups to the carrier, preferably by chemical binding, particularly preferably by covalent binding.

The biocompatible polymer comprises functional groups, preferably carboxyl groups, the functional groups having an unbalanced molecule charge preferably on account of chemical activation, the functional groups being preferably matched to the detection receptors.

The biocompatible polymer has hydrophilic properties and is preferably a hydrogel.

The biocompatible polymer comprises chemically and/or enzymatically cleavable groups which facilitate the detachment of the ligands. The chemically and/or enzymatically cleavable groups are preferably the functional groups to which the detection receptors are bound.

The biocompatible polymer comprises saturated atom groups and covalently bound receptors to prevent undesired interactions with blood components and the binding of non-specific cells and molecules.

The biocompatible polymer is arranged in a cavity of the carrier. A cavity of the carrier can thereby be used for the enrichment of ligands. The ligands are there optimally protected from abrasion.

The biocompatible polymer is crosslinked.

The biocompatible polymer comprises and/or forms the functional surface. The functional surface is preferably located on the surface of the biocompatible polymer. The biocompatible polymer can be directly equipped with the detection receptors.

In yet another advantageous configuration of the invention the functional surface is coated with a protective layer, the protective layer preferably meeting at least one of the following requirements:

The protective layer is soluble in liquids, particularly in body fluids, preferably in blood. The functional surface can thereby be exposed automatically as soon as the protective layer gets into contact with the sample liquid.

The protective layer is biocompatible. This substantially prevents defense reactions of the body during the in vivo use of the detection device.

The protective layer is organically crystalline and comprises at least one of the following constituents: alginates, preferably high-purity alginates, polyethylene glycols, cyclic and non-cyclic oligosaccharides, polysaccharides, antioxidative amino acids, proteins or vitamins. Such constituents are biocompatible and easily soluble.

It may be useful when the detection receptors are operatively connected preferably via linkers or organic functional groups to the functional surface, preferably to the carrier and/or the biocompatible polymer, preferably by chemical binding, particularly preferably by covalent binding. This substantially prevents a non-specific adsorption on the functional surface.

A further independent aspect of the invention refers to a detection device according to at least one of the preceding claims, produced by:
providing a carrier;
chemical activation of the carrier by chemical, preferably covalent, binding of the detection receptors directly or via a biocompatible polymer to functional groups of the carrier, preferably to organic functional groups of the carrier, preferably via sulfur- and/or nitrogen-containing compounds.

The detection device can comprise each of the aforementioned features.

Yet another independent aspect of the invention refers to the use of a detection device according to any one of the preceding claims for the invasive enrichment of sample material, for the elimination of drugs, for the elimination of radioactive tracers, for the elimination of magnetic beads, for obtaining tumor markers or biomarkers and/or for the elimination of toxins, or for the enrichment of cells, comprising embryonic trophoblasts, disseminated tumor cells, particularly of hematogenically metastasizing tumors. The aforementioned advantages can be achieved thereby.

Yet another independent aspect of the invention refers to a method for the enrichment of sample material by using a detection device according to at least one of the preceding claims, the method comprising the following steps:
exposing the functional surface to a sample liquid;
enriching sample material, preferably cells, DNA, RNA, proteins, peptides, synthetic molecules, on the detection receptors, and
removing the sample liquid.

The detection device can comprise each of the aforementioned features.

Preferred developments of the invention ensue from combinations of the sub-claims or partial features mentioned therein.

DETAILED DESCRIPTION OF THE PREFERRED EMBODIMENTS

The preferred embodiments of the invention are described hereinafter with reference to the attached drawings.

First Embodiment

The detection device 1 according to the invention according to the first embodiment is a biofunctionalized medical detection catheter for the invasive (in vivo) enrichment of rare cells, biomolecules or drugs. Such a detection catheter is also called medical nano-catheter (MN-C).

Figure 1:
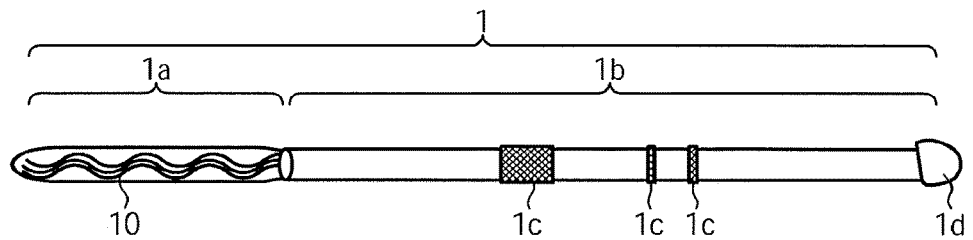
FIG. 1 is a schematic illustration of a detection device according to the invention in the form of a stylet.

FIG. 1 is a schematic illustration of the detection catheter. The functionalized part 1a has a length of about 2 cm and comprises the functional surface 10 equipped with detection receptors. The non-functionalized part 1b has a length of about 14 cm and comprises markings 1c for application control and, at the end, a hemisphere 1d as protection from injury for the user. The functionalized part 1a and the non-functionalized part 1b of the catheter 1 are joined to form a stylet.

Figure 2:
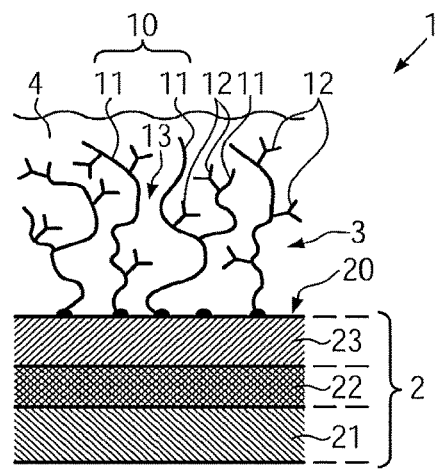
FIG. 2 shows the layered structure of a functionalized part of the detection device.

FIG. 2 shows the layered structure of the functionalized part 1a of the detection catheter.

Figure 3:
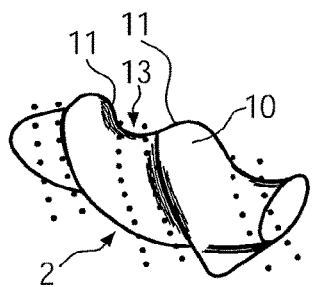
FIG. 3 is a schematic illustration of a screw-shaped carrier.

The carrier 2 has e.g. a screw-shaped structure, as shown in FIG. 3. In the macroscopic or visible range the thread of the carrier 2 forms a three-dimensionally structured functional surface 10 with mutually facing functional sections 11 and with a space 13 that can be filled with a sample liquid. According to the principle of a stent spiralized wires can be matched to the diameter of a blood vessel in which temporary placement is to be carried out. In contrast to a cylindrical catheter 1 the spiralized form affords a less pronounced constriction of the blood vessel. The recesses or thread depths prevent abrasion of the detected molecules or cells (outlined by dotted lines) caused by removal.

Figure 4:
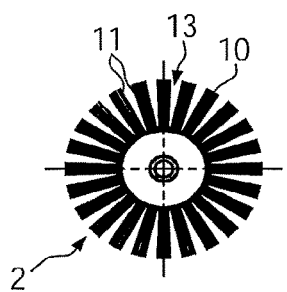
FIG. 4 is a cross-sectional view of a brush-like carrier.
Figure 5:
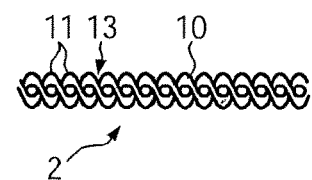
FIG. 5 is a schematic illustration of a helical carrier.

The form of the catheter 1 may have any desired design and depends on the application. The catheter 1 can e.g. also comprise a helical or brush-like carrier 2 according to FIG. 4 or FIG. 5. The brush-like carrier 2 according to FIG. 4 can be constructed from one or plural metal, glass, Teflon or plastic polymer filaments, wherein in the macroscopic or visible range the filaments form a three-dimensionally structured functional surface 10 with mutually facing functional sections 11 and spaces 13 which can be filled with sample liquid. The helical carrier 2 according to FIG. 5 can consist of a strand having one or plural metal wires. A functional surface 10 which is three-dimensionally structured in the macroscopic range and includes mutually facing functional sections 11 and spaces 13 that can be filled with sample liquid is formed in this case by the flanks of the helix.

Thanks to the functional surface 10 which is three-dimensionally structured in the visible range the carrier 2 is able to reduce constrictions in the bloodstream and to change the laminar blood flow by way of the special geometry in such a manner that in comparison with a cylindrical catheter the probability of binding target molecules and target cells is greater by the factor 2.

A substrate 21 of medical high-grade steel wire with a diameter of about 0.5 mm gives the carrier 2 its visible structure. The substrate 21 may comprise one or plural coatings 22, 23. Preferably, the substrate 21 is coated with a gold coating 22 having a thickness of from 0.5 µm to 1.0 µm, which is applied by galvanic processes, ceramic processes, cementation or vapor deposition. The substrate 21 can further be coated with a biocompatible dye to reduce autofluorescence of the basic material during microscopic analysis.

The chemical activation of the carrier 2 takes place via an affinity reaction mostly by sulfur- or nitrogen-containing compounds to which, in turn, specific detection receptors 12 can be bound directly or via polymer chains.

Preferably, a covalent secondary layer consisting of a functional biocompatible polymer 3 is applied to the carrier 2 by means of wet chemical or physical processes. The layer thickness can be 1 µm to 2 µm. The carrier 2 is thereby chemically activated. Owing to the surface finishing and chemical activation specific antibodies, particularly monoclonal antibodies of murine origin, chimeric antibodies, humanized antibodies, or fragments of said antibodies or amino acid structures or nucleic acid structures or synthetic structures with specific affinity to cell surfaces or molecules can be covalently bound as detection receptors 12.

Especially in the case of a complex sample liquid, such as blood, not only a permanent binding of the detection receptors 12 while maintaining the biological function, but also an efficient suppression of non-specific adsorption processes are of decisive importance to the selective binding of the ligands.

Here an interlayer 23 has the function to ensure an efficient shielding of the surface of the substrate 21 and to simultaneously provide the functional groups for binding the biocompatible polymer layer 3 at an adequate density. The interlayer system thus forms a bonding agent between the gold coating 22 of the substrate 21 and the biocompatible polymer layer 3.

The biocompatible polymer 3 is preferably a hydrogel with carbon-containing long branched macromolecules which have a great number of functional groups, e.g. carboxyl groups or polycarboxylates. The type of the functional groups depends on the molecular properties of the specific detection receptors 12. The biocompatible hydrogel thereby ensures the permanent covalent binding of the detection receptors 12 while maintaining the biological function and simultaneously prevents impairment of the detection function of the detection receptors 12 by non-specific adsorption phenomena. Hydrogels are three-dimensionally crosslinked hydrophilic polymers that absorb liquids such as water, but are not soluble therein. Main constituents of the hydrogel are polyacrylic acid (PAA) and polyethylene glycol (PEG). Property profiles can be customized in response to the desired requirements or fields of application through an appropriate selection of the monomer units, the crosslinking degree and the crosslinking density. An essential property is biocompatibility, i.e. compatibility of the hydrogel with the living tissue. Due to the branched polymer chains of the biocompatible polymer 3 the thrombogenic effect during invasive application is also suppressed. Due to chemical activation the functional groups receive an unbalanced molecule charge that makes it possible to electrostatically attract detection receptors 12 from a solution and to covalently bind them. The detection receptors 12 which are permanently immobilized on the polymer layer 3 serve the specific binding of the ligands or the target molecules and target cells through their surface antigens, thereby enabling the function of the detection device 1. This biocompatible polymer 3 can additionally contain chemically or enzymatically cleavable groups to simplify the quantitative recovery of bound target molecules or cells.

The branched molecular structures of the biocompatible polymer 3 form a functional surface 10 which is three-dimensionally structured in the microscopic range and includes mutually facing functional sections 11 and spaces which can be filled with sample liquid, as is schematically shown in FIG. 1. While the surface of the carrier 2 which is three-dimensionally structured in the macroscopic or visible range (cf. FIGS. 3, 4 and 5) conducts the sample liquid in an advantageous manner over the functional part 1a of the catheter 1, the functional surface 10 of the biocompatible polymer 3 which is three-dimensionally structured in the microscopic range (cf. FIG. 2) slows down the flow of the sample liquid in the area of the interface and promotes the enrichment of the ligands on the detection receptors 12.

For preserving and for protection against the conditions of final sterilization and for radiation protection and for the stability of the product a biocompatible protective layer (tertiary layer or stabilizer layer) 4 is applied over the biocompatible polymer 3. This protective layer 4 dries up over the secondary layer and forms a dense network of crystalline structures and stabilizes and thereby preserves the functional part 1a of the catheter 1. The protective layer 4 is not covalently bound. The protective layer 4 dissolves in the bloodstream and exposes the functional surface 10 of the catheter. Alternatively, the protective layer 4 can be washed off with sterile water prior to use.

The protective layer 4 can comprise high-purity alginates, polyethylene glycols, cyclic and non-cyclic oligosaccharides and polysaccharides, antioxidative amino acids, proteins and vitamins. The protective layer 4 preferably consists of a biocompatible high-viscosity polysaccharide which serves as a medium for added amino acids, proteins, vitamins and stabilizing polysaccharides. The high viscosity affords a quick wettability of the surface. The attached protective layer 4 adheres to the secondary coating and prevents the penetration of foreign substances during storage.

In comparison with the specific ligands the added amino acids, proteins and vitamins are present in increased concentrations and thereby able to prevent the likelihood of damage to the target molecules by radical molecules or charge carriers and to reestablish chemical bonds destroyed by recombination processes.

The finished catheter 1 is packed in a low-germ environment. Final sterilization is carried out by means of gamma irradiation at a radiation dose of 25 kGy. The catheter 1 is intended for single use.

Use of the Detection Device

The catheter 1 produced according to the invention with refined functional surface 10 and with coupled detection receptors 1 is suited for obtaining rare cells from the bloodstream. This includes the following examples of use:

Obtaining embryonic trophoblasts from the maternal blood circulation with e.g. specific antibody fragments (F(ab) fragments) and murine monoclonal antibodies (IgG) which can detect the cell surface protein HLA-G which is typical of trophoblasts.

Obtaining disseminated tumor cells, particularly hematogenically metastasizing tumors e.g. with the humanized antibody anti-EpcCAM which detects the cell surface protein EpCAM typical of many cancer cells.

A preferred use of the detection device 1 lies in prenatal and cancer diagnostics. The detection device 1 can e.g. be used for isolating fetal cells or tumor cells circulating in the bloodstream of pregnant women or cancer patients. For application the detection device 1 is introduced into the vein via a suitable, commercially available Braunüle cannula system and is applied into the venous blood circulation. The retention time in the vein can be about 30 min. After removal of the detection device 1 from the bloodstream the cells bound on the detection device 1 are further enriched by means of selective laboratory diagnostics and characterized by molecular or cell biology.

The aim of the minimally invasive procedure to be carried out is the selection of fetal cells or tumor cells from the blood. Due to the low cell concentration of the cells in the blood a blood withdrawal of about 0.5 l would be needed to achieve the desired target cell number. This is however ruled out under medical aspects.

In prenatal diagnostics a possible chromosome aberration (e.g. trisomy 21 (Down syndrome)) is to be detected with the help of the fetal cells contained in the maternal blood. The Down syndrome has so far been diagnosed in a safe way prenatally only by invasive procedures, each posing an abortion risk of 1%: chorionic villus sampling between the $11^{th}$ and $14^{th}$ week of pregnancy and amniocentesis from the $15^{th}$ week of pregnancy. By contrast the method according to the invention, which will be usable from the $9^{th}$ week of pregnancy, poses no risk for the fetuses and can be used in first-trimester screening. Hence, amniocentesis can be omitted.

Fetal trophoblast cells from the placenta can be detected in the maternal blood circulation starting from the $6^{th}$ week of pregnancy. There are only about 2 to 5 of these cells per ml of maternal blood. These trophoblast cells have a membrane-bound HLA-G complex (antigen) which binds to specific antibodies. Preferably, a specific HLA-G antibody is used as the detection receptor 12 which only reacts with the membrane-bound HLA-G (antigen) and is thus only to capture the desired fetal cells from the maternal blood.

Carcinoma tumor cells can be enriched with the EpCAM antibody (against the EpCAM antigen) which is humanized in its constant domains and covalent and the hydrogel is bound.

Second Embodiment

The detection device according to the invention according to the second embodiment refers to an in vitro detection device which comprises a porous or filamentous functional surface 10 and is able to enrich cells or molecules from body fluids or other liquid test material. The same reference numerals are used for similar features as in the first embodiment and reference is made to the above description.

The detection device 1 comprises a carrier 2 with a sealed cavity through which the sample liquid is passed. The cavity contains a porous or filamentous matrix, preferably a biocompatible polymer 3 or a polymer foam. The aforementioned detection receptors 12 can be bound directly or via linkers covalently to the surface of said porous or filamentous matrix. In the macroscopic and/or microscopic range the pore walls or filaments form a three-dimensionally structured functional surface 10 with mutually facing functional sections 11 and spaces 13 which can be filled with sample liquid. The surface increase created thereby increases the number of available detection receptors 12 and thereby provides for an improved enrichment of the target molecules or target cells. The pore size or the thickness and amount of the filaments of the matrix are variable and can be adapted to the type of the target molecules or target cells to be detected.

The coating of the detection device 1 is analogous to the catheter coating according to the first embodiment with the difference that the carrier 2 consists mainly of biocompatible plastics, such as polyurethane, polyethylene, Teflon or polypropylene. The carrier 2 can be functionalized by wet chemical or physical processes. The functional surface 10 of the matrix can comprise activatable organic polymers and functional groups.

Said detection device is suited for the enrichment or concentration of cells or biomolecules from body fluids or other liquid analytical samples. The liquid test samples are applied into the detection device 1 or are immediately introduced by means of Luer-Lock withdrawing or sampling systems. The isolated and enriched material can immediately be supplied to a downstream diagnostic device, e.g. via lab-on-chip technology.

This detection device 1 is distinguished by a very simple handling owing to its design and can be used without any great expenditure of time by means of a kit in any diagnostic or clinical device or facility.

The invention claimed is:

1. A detection device for the in vivo and/or in vitro enrichment of sample material, comprising a biocompatible polymer comprising saturated atom groups and covalently bound ligands and/or receptors that forms a functional surface, wherein the functional surface has a three-dimensional and at least partly spiral, screw-shaped or helical structure with mutually facing functional sections which form at least one space configured to be filled with a sample liquid, wherein the detection device comprises a carrier to which the biocompatible polymer is operationally connected via functional groups, wherein the carrier comprises a coating of metal that is applied by means of a galvanic process and a biocompatible dye.

2. The detection device according to claim 1, wherein the functional surface is three-dimensionally structured in a macroscopic and/or in a microscopic range.

3. The detection device according claim 1, wherein the space is channel-shaped at least in sections, comprising a plurality of spaces forming a network of channels.

4. The detection device according to claim 1, wherein the functional surface is formed with elevations, depressions and/or ramifications and/or has at least in part a worm-shaped, undulated, filamentous, brush-like, comb-like, meshed, porous, sponge-like or similar structure.

5. The detection device according to claim 1, wherein the detection receptors are selected from among a group consisting of:
    antibodies, antibody fragments, amino acid structures, nucleic acid structures and/or synthetic structures with specific affinity to cell surfaces, monoclonal antibodies of murine origin, chimeric antibodies or humanized antibodies, HLA-G antibodies, and EpCAM antibodies.

6. The detection device according to claim 1, wherein the detection device is formed at least in sections as a guide wire, stent and/or catheter.

7. The detection device according to claim 1, wherein the detection device comprises a functionalized section provided with the functional surface and a non-functionalized section which are both joined to form a stylet.

8. The detection device according to claim 1, wherein a non-functionalized section comprises a marking for application control and/or a rounded end as protection from injury.

9. The detection device according to claim 1, wherein the detection device comprises a carrier which meets at least one of the following requirements:
    a. The surface of the carrier is formed with elevations, depressions and/or ramifications and/or has at least in part a spiral, screw-shaped, worm-shaped, undulated, helical, filamentous, brush-like, comb-like, meshed, porous, sponge-like or similar structure;
    b. The carrier comprises a substrate which is formed with elevations, depressions and/or ramifications and/or has at least in part a spiral, screw-shaped, worm-shaped, undulated, helical, filamentous, brush-like, comb-like, meshed, porous, sponge-like or similar structure;
    c. The carrier comprises a coating of metal of the $10^{th}$ or $11^{th}$ group of the Periodic Table of Elements;
    d. The carrier comprises organic functional groups;
    e. The carrier is configured as a solid body or as a hollow body;
    f. The carrier is made from a biocompatible material;
    g. The carrier comprises metal, glass, plastic, a polymer, a plastic based on organic polymers, or a combination of said materials;
    h. The carrier comprises and/or forms the functional surface.

10. The detection device according to claim 1, wherein the biocompatible polymer meets at least one of the following specifications:
    a. The biocompatible polymer is formed as a coherent polymer layer;
    b. The biocompatible polymer has a three-dimensional, filamentous and/or porous structure;
    c. The biocompatible polymer comprises a three-dimensional, filamentous, and/or porous surface;
    d. The biocompatible polymer has a carbon-containing, branched molecular structure;
    e. The biocompatible polymer comprises functional groups, the functional groups having an unbalanced molecule charge, the functional groups being matched to the detection receptors;
    f. The biocompatible polymer has hydrophilic properties;
    g. The biocompatible polymer comprises chemically and/or enzymatically cleavable groups;
    h. The biocompatible polymer comprises saturated atom groups and covalently bound ligands and receptors;
    i. The biocompatible polymer is arranged in a cavity of the carrier;
    j. The biocompatible polymer is crosslinked.

11. The detection device according to claim 1, wherein the functional surface is coated with a protective layer, the protective layer optionally meeting at least one of the following requirements:
    a. The protective layer is soluble in liquids;
    b. The protective layer is biocompatible;
    c. The protective layer is organically crystalline and comprises at least one of the following constituents: alginates, polyethylene glycols, cyclic and non-cyclic oligosaccharides, polysaccharides, antioxidative amino acids, proteins or vitamins.

12. The detection device according to claim 1, wherein the detection receptors are operatively connected via linkers or organic functional groups to the functional surface by chemical binding.

13. A detection device for the in vivo and/or in vitro enrichment of sample material, comprising a biocompatible polymer comprising saturated atom groups and covalently bound ligands and/or receptors that forms a functional surface wherein the functional surface has a three-dimensional and at least partly spiral, screw-shaped or helical structure with mutually facing functional sections which form at least one space configured to be filled with a sample liquid, wherein the detection device comprises a carrier to which the biocompatible polymer is operatively connected via functional groups by chemical binding, wherein the carrier comprises a coating of metal that is applied by means of a galvanic process, and wherein the functional surface is coated with a protective layer, wherein the protective layer is soluble in liquids and biocompatible.

* * * * *